United States Patent
Zhang

(10) Patent No.: US 10,380,406 B2
(45) Date of Patent: Aug. 13, 2019

(54) FINGERPRINT SENSOR, METHOD FOR MANUFACTURING FINGERPRINT SENSOR, AND TERMINAL

(71) Applicant: Guangdong Oppo Mobile Telecommunications Corp., Ltd., Dongguan, Guangdong (CN)

(72) Inventor: Wenzhen Zhang, Guangdong (CN)

(73) Assignee: Guangdong Oppo Mobile Telecommunications Corp., Ltd., Dongguan (CN)

( * ) Notice: Subject to any disclaimer, the term of this patent is extended or adjusted under 35 U.S.C. 154(b) by 117 days.

(21) Appl. No.: 15/667,931

(22) Filed: Aug. 3, 2017

(65) Prior Publication Data

US 2018/0053037 A1 Feb. 22, 2018

(30) Foreign Application Priority Data

Aug. 16, 2016 (CN) .......................... 2016 1 0675360
Aug. 16, 2016 (CN) ...................... 2016 2 0890356 U

(51) Int. Cl.
*G06K 9/00* (2006.01)
*A61B 5/117* (2016.01)
(Continued)

(52) U.S. Cl.
CPC .......... *G06K 9/00053* (2013.01); *A61B 5/117* (2013.01); *G01B 11/24* (2013.01); *H01L 24/95* (2013.01); *H04M 1/26* (2013.01); *H05K 3/0058* (2013.01); *A61B 5/00* (2013.01); *G06F 1/1684* (2013.01); *G06K 9/00* (2013.01)

(58) Field of Classification Search
CPC .......... G06K 9/00013; G06K 9/00053; G06K 9/0002; G06K 9/0004
See application file for complete search history.

(56) References Cited

U.S. PATENT DOCUMENTS 7,030,860 B1 * 4/2006 Hsu .................. G06F 3/044
178/18.06
8,068,186 B2 * 11/2011 Aufderheide .......... G06F 3/044
349/12
(Continued)

FOREIGN PATENT DOCUMENTS

CN 103052293 A 4/2013
CN 104731415 A 6/2015
(Continued)

OTHER PUBLICATIONS

Extended European Search Report issued in corresponding European Application No. 17182045.9 dated Feb. 1, 2018 (8 pp).
International Search Report issued in corresponding International Application No. PCT/CN2017/094072 dated Oct. 24, 2017 (12 pp).

*Primary Examiner* — Utpal D Shah
(74) *Attorney, Agent, or Firm* — Young Basile Hanlon & MacFarlane, P.C.

(57) ABSTRACT

A fingerprint sensor, a terminal, and a method for manufacturing a fingerprint sensor are provided. The fingerprint sensor includes a chip unit and a first adhesive layer. The chip unit includes a first surface and a second surface opposite to the first surface. The first surface is configured to receive a touch operation. The first adhesive layer is directly or indirectly attached to the second surface in a peelable manner.

10 Claims, 9 Drawing Sheets

(51) Int. Cl.
*G01B 11/24* (2006.01)
*H01L 23/00* (2006.01)
*H04M 1/26* (2006.01)
*H05K 3/00* (2006.01)
A61B 5/00 (2006.01)
G06F 1/16 (2006.01)

(56) References Cited

U.S. PATENT DOCUMENTS

| | | | |
|---|---|---|---|
| 9,152,838 B2* | 10/2015 | Wickboldt | H05K 1/189 |
| 9,268,435 B2* | 2/2016 | Solven | G06F 3/0416 |
| 2007/0067640 A1 | 3/2007 | Murata et al. | |
| 2009/0001611 A1 | 1/2009 | Matsumura et al. | |
| 2014/0270418 A1* | 9/2014 | Lin | G06K 9/00053 |
| | | | 382/124 |
| 2016/0103526 A1* | 4/2016 | Sohn | G06F 3/044 |
| | | | 345/174 |
| 2017/0004343 A1* | 1/2017 | Xie | G06F 3/0416 |
| 2017/0116458 A1* | 4/2017 | Liu | G06K 9/00013 |
| 2017/0177921 A1* | 6/2017 | Fornof | G06K 9/00046 |
| 2018/0145102 A1* | 5/2018 | Wang | G06K 9/0002 |

FOREIGN PATENT DOCUMENTS

| | | |
|---|---|---|
| CN | 204650546 U | 9/2015 |
| CN | 105373778 A | 3/2016 |
| EP | 2621254 A1 | 7/2013 |
| WO | 2016093669 A1 | 6/2016 |

\* cited by examiner

FINGERPRINT SENSOR, METHOD FOR MANUFACTURING FINGERPRINT SENSOR, AND TERMINAL

CROSS-REFERENCE TO RELATED APPLICATION(S)

This application claims priority to Chinese Patent Application No. 201610675360.0, filed on Aug. 16, 2016, and Chinese Patent Application No. 201620890356.1, filed on Aug. 16, 2016, the content of both of which are hereby incorporated by reference in their entireties.

TECHNICAL FIELD

The present disclosure relates to the field of electronic devices, and particularly to a fingerprint sensor, a method for manufacturing a fingerprint sensor, and a terminal.

BACKGROUND

At present, fingerprint sensors are widely used in terminals, for example, mobile phones, tablet computers, and so on. Generally, the fingerprint sensor includes a chip unit secured to one or more other elements of the fingerprint sensor, and cannot be disengaged from the other elements. Thus, when the chip unit needs to be replaced, the whole fingerprint sensor needs to be replaced, thereby increasing the cost.

BRIEF DESCRIPTION OF THE DRAWINGS

In order to illustrate the technical solutions of the implementations of the present disclosure more clearly, the accompanying drawings used in the description of the implementations will be briefly described, it will be apparent that the accompanying drawings described in the following are some implementations of the present disclosure, and it will be apparent to those skilled in the art that other drawings can be obtained from the accompanying drawings without any creative effort.

DETAILED DESCRIPTION

The present disclosure will now be described in further detail with reference to the accompanying drawings and implementations, in which the objects, solutions, and advantages of the present disclosure will become more apparent. It is to be understood that specific implementations described herein are merely illustrative of the present disclosure and are not intended to limit the present disclosure.

Figure 1:
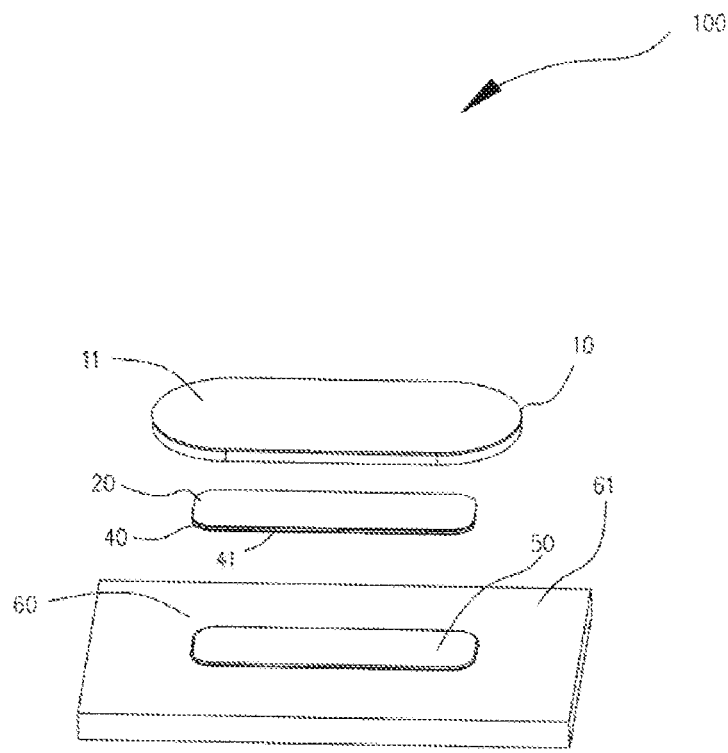
FIG. 1 is an exploded view of a fingerprint sensor in accordance with an implementation of the present disclosure.
Figure 2:
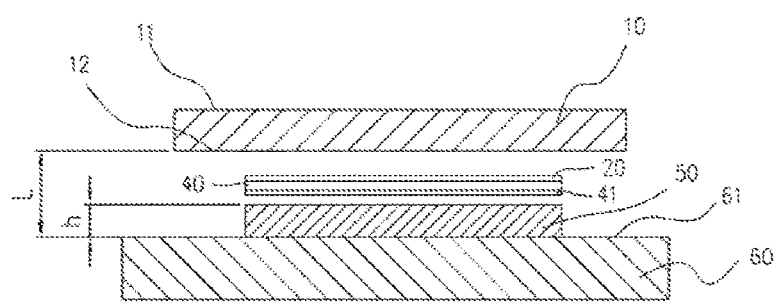
FIG. 2 is a sectional view of the fingerprint sensor of FIG. 1.

FIG. 1 and FIG. 2 illustrate a fingerprint sensor 100 according to a first implementation of the present disclosure. The fingerprint sensor 100 may be applied to a terminal 200 (see FIG. 15). The terminal 200 may be a mobile phone, a tablet, a laptop, a handheld computer, a mobile internet device (MID), or wearable equipment such as a smart watch, a smart bracelet, and a pedometer or others. Terminals in the present disclosure are not limited to common terminals, but may also be automated teller machines (ATM), ticket machines, entrance guard machines, medical equipment, or other terminals equipped with fingerprint recognition function.

The fingerprint sensor 100 may include a chip unit 10 and a first adhesive layer 20. The chip unit 10 may have a first surface 11 and a second surface 12 opposite to the first surface 11. The first surface 11 is configured to receive a touch operation. The first adhesive layer 20 is attached to the second surface 12 in a peelable manner. The first adhesive layer 20 is peelable, that is, when the second surface 12 is attached to one or more other elements (hereinafter, only one other element is referred to for illustration) of the terminal 200 via the first adhesive layer 20, the chip unit 10 can be peeled off from the other implementation of the terminal 200.

In the implementation, the chip unit 10 is attached to the other element via the first adhesive layer 20, and the first adhesive layer 20 is peelable, thus, when the fingerprint sensor 100 needs to be replaced, the chip unit 10 can be detached from the other element and is replaced by another chip unit, thereby reducing cost of the fingerprint sensor 100.

The chip unit 10 may be an elliptical plate. It can be understood that the chip unit 10 may be connected to a housing 30 (see FIG. 15) of the terminal 200. The chip unit 10 may be directly connected to the housing 30, and may also be connected to the housing 30 via one or more other components. For example, the housing 30 may define a hole 31 (see FIG. 15). A periphery of the chip unit 10 may be detachably connected to an inner side of the hole 31. In other implementations, the chip unit 10 may be a circle plate, a rectangular plate, or the like.

The first adhesive layer 20 may be made from synthetic resin and polymer additives. When an external force is applied to the chip unit 10 to peel off the chip unit 10, the second surface 12 may be separated from the first adhesive layer 20, or the second surface 12 and the first adhesive layer 20 together may be separated from the other element.

In the first implementation, the first adhesive layer 20 may be covered a portion of the second surface 12. Certainly, in other implementations, the first adhesive layer 20 may also be covered the whole second surface 12. The chip unit 10 is attached to the other element via the first adhesive layer 20. When an external force is applied to the chip unit 10 to peel off the chip unit 10, the chip unit 10 can be directly separated from the first adhesive layer 20, or the chip unit 10 and the first adhesive layer 20 together are separated from the other element.

Furthermore, the fingerprint sensor 100 may further include a substrate layer 40. The substrate layer 40 may be made from a polyethylene terephthalate film. The substrate layer 40 may have a first side facing the chip unit 10, and a second side opposite to the first side. The first adhesive layer 20 is coated on the first side, and a second adhesive layer 41 is coated on the second side. That is, the first adhesive layer 20 is provided between the substrate layer 40 and the chip unit 10, and the second adhesive layer 41 is provided between the substrate layer 40 and the other element. The first adhesive layer 20 is coated on the substrate layer 40 via a thermal processing process. The first adhesive layer 20 and the substrate layer 40 may cooperatively form a release film. Since the first adhesive layer 20 is coated on the substrate layer 40, the first adhesive layer 20 can be protected. The second adhesive layer 41 may be made from superglue. The second adhesive layer 41 has glutinosity greater than that of the first adhesive layer 20. When an external force is applied to the chip unit 10 to peel off the chip unit 10, since the glutinosity of the first adhesive layer 20 is greater than that of the second adhesive layer 41, the chip unit 10 is separated from the first adhesive layer 20, and the first adhesive layer 20 and the substrate layer 40 are attached to the other element due to the second adhesive layer 41. Certainly, in other implementations, the first adhesive layer 20 may be provided between the substrate layer 40 and the other element, and the second adhesive layer 41 may be provided between the chip unit 10 and the substrate layer 40.

Furthermore, the fingerprint sensor 100 may further include a support element 50. The support element 50 may be attached to the substrate layer 40 to support the chip unit 10. The support element 50 may be an adhesive layer, and the support element 50 may be directly coated on the substrate layer 40. Thus, when an external force is applied to the chip unit 10 to peel off the chip unit 10, the chip unit 10, together with the substrate layer 40 and the first adhesive layer 20, may be separated from the support element 50, or the chip unit 10, together with the substrate layer 40, the first adhesive layer 20, and the support element 50 may be separated from the other element.

The periphery of the chip unit 10 is made from brittle material, and if the second surface 12 of the chip unit 10 is impending, when the chip unit 10 is pressed, the periphery of the chip unit 10 may be broken. Thus, by means of setting the support element 50 to support the chip unit 10, when the chip unit 10 is pressed, the periphery of the chip unit 10 may not be broken due to the support of the support element 50, thereby protecting the chip unit 10, accordingly protecting the fingerprint sensor 100.

Figure 3:
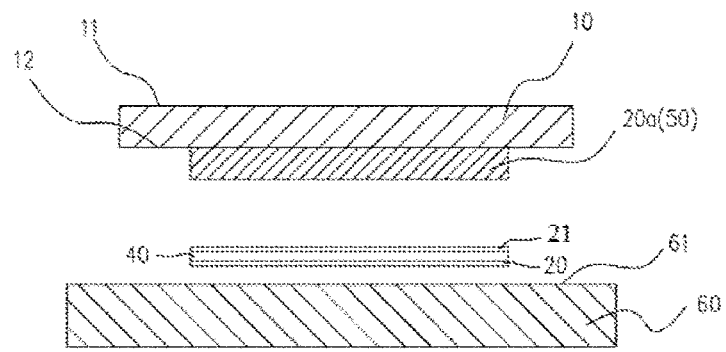
FIG. 3 is a sectional view of a fingerprint sensor in accordance with a second implementation of the present disclosure.

FIG. 3 illustrates a fingerprint sensor according to a second implementation of the present disclosure. The fingerprint sensor in the second implementation is substantially the same as that in the first implementation, and a difference between the fingerprint sensor in the first implementation and the fingerprint sensor in the second implementation is that, in the second implementation, the second surface 12 is provided with an isolation element 20a, the first side of the substrate layer 40 is provided with a third adhesive layer 21, and the second side of the substrate layer 40 is provided with the first adhesive layer 20. The third adhesive layer 21 has glutinosity which is substantially the same as that of the first adhesive layer 20 or greater than or less than that of the first adhesive layer 20. The third adhesive layer 21 is attached to a side of the isolation element 20a away from the chip unit 10. When an external force is applied to the chip unit 10 to peel off the chip unit 10, the chip unit 10 and the isolation element 20a together are separated from the first adhesive layer 20, or the chip unit 10, the isolation element 20a, and the first adhesive layer 20 together are separated from the other element. It can be understood that the isolation element 20a may be a circuit board, a pad, a connector, or other.

Alternatively, the support element 50 may be used to replace the isolation element 20a, thus the support element 50 is arranged between the substrate layer 40 and the chip unit 10. The support element 50 is attached to the substrate layer 40 via the third adhesive layer 21. The support element 50 is fixed to the chip unit 10. When an external force is applied to the chip unit 10 to peel off the chip unit 10, the chip unit 10 and the support element 50 together may be separated from the substrate layer 40.

In the second implementation, the substrate layer 40 is attached to the isolation element 20a via the third adhesive layer 21, and the substrate layer 40 is attached to the other element via the first adhesive layer 20. Certainly, in other implementations, the substrate layer 40 may be attached to the isolation element 20a via the first adhesive layer 20, and the substrate layer 40 may be attached to the other element via the second adhesive layer 41, alternatively, the substrate layer 40 may be attached to the isolation element 20a via the second adhesive layer 41, and the substrate layer 40 may be attached to the other element via the first adhesive layer 20.

Figure 4:
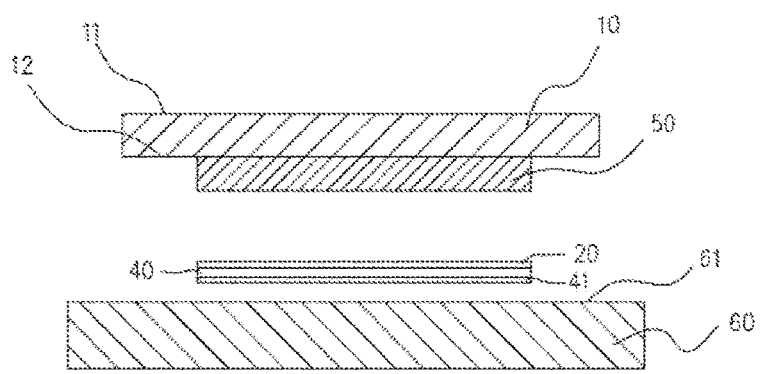
FIG. 4 is a sectional view of a fingerprint sensor in accordance with a third implementation of the present disclosure.

FIG. 4 illustrates a fingerprint sensor according to a third implementation of the present disclosure. The fingerprint sensor in the third implementation is substantially the same as that in the first implementation, and a difference between the fingerprint sensor in the first implementation and the fingerprint sensor in the third implementation is that, in the third implementation, the support element 50 is provided between the substrate layer 40 and the chip unit 10, that is, the support element 50 is directly fixed to the second surface 12, and the support element 50 is attached to the substrate layer 40 via the first adhesive layer 20. When an external force is applied to the chip unit 10 to peel off the chip unit 10, the chip unit 10 and the support element 50 together are separated from the substrate layer 40.

Figure 5:
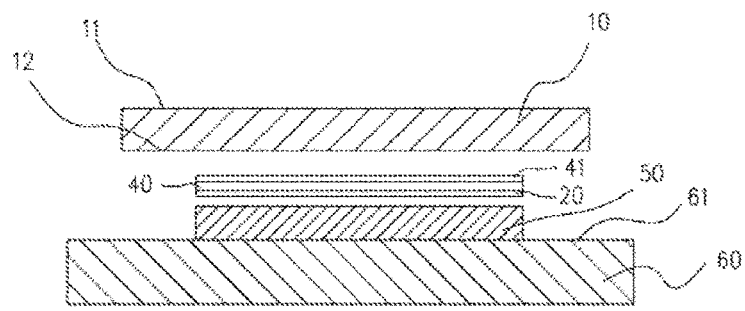
FIG. 5 a sectional view of a fingerprint sensor in accordance with a fourth implementation of the present disclosure.

FIG. 5 illustrates a fingerprint sensor according to a fourth implementation of the present disclosure. The fingerprint sensor in the fourth implementation is substantially the same as that in the first implementation, and a difference between the fingerprint sensor in the first implementation and the fingerprint sensor in the fourth implementation is that, in the fourth implementation, the substrate layer 40 is attached to the chip unit 10 via the second adhesive layer 41, and is attached to the support element 50 via the first adhesive layer 20. Thus, when an external force is applied to the chip unit 10 to peel off the chip unit 10, the chip unit 10 and the substrate layer 40 together are separated from the support element 50.

Figure 6:
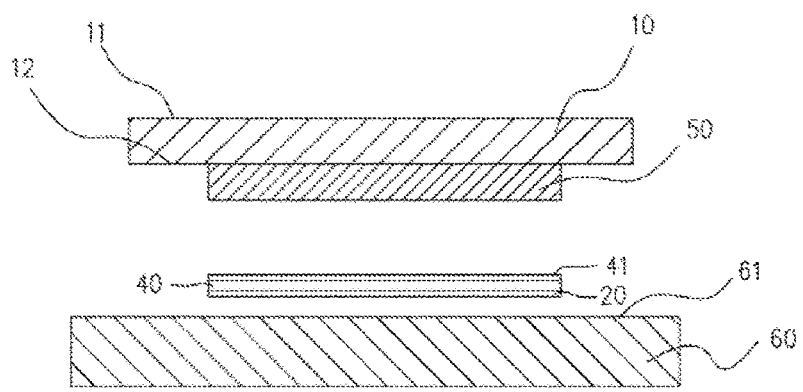
FIG. 6 is a sectional view of a fingerprint sensor in accordance with a fifth implementation of the present disclosure.

FIG. 6 illustrates a fingerprint sensor according to a fifth implementation of the present disclosure. The fingerprint sensor in the fifth implementation is substantially the same as that in the first implementation, and a difference between the fingerprint sensor in the first implementation and the fingerprint sensor in the fifth implementation is that, in the fifth implementation, the support element 50 is fixed to the second surface 12, the substrate layer 40 is provided at a side of the support element 50 away from the chip unit 10, the substrate layer 40 is attached to the support element 50 via the second adhesive layer 41, and is attached to the other element via the first adhesive layer 20.

Figure 7:
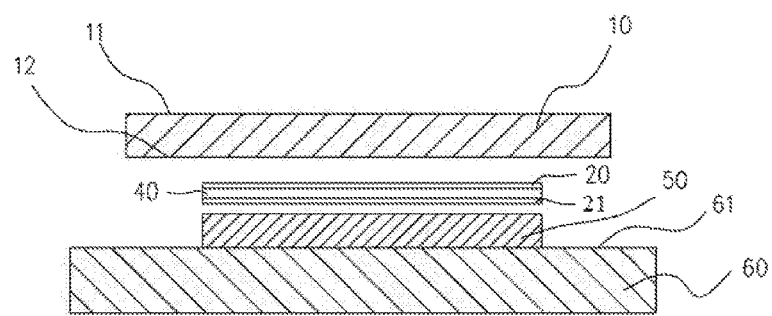
FIG. 7 is a sectional view of a fingerprint sensor in accordance with a sixth implementation of the present disclosure.

FIG. 7 illustrates a fingerprint sensor according to a sixth implementation of the present disclosure. The fingerprint sensor in the sixth implementation is substantially the same as that in the first implementation, and a difference between the fingerprint sensor in the first implementation and the fingerprint sensor in the sixth implementation is that, in the sixth implementation, the second side of the substrate layer 40 is provided with the third adhesive layer 21. That is, the substrate layer 40 is attached to the chip unit 10 via the first adhesive layer 20, and is attached to the support element 50 via the third adhesive layer 21.

Figure 8:
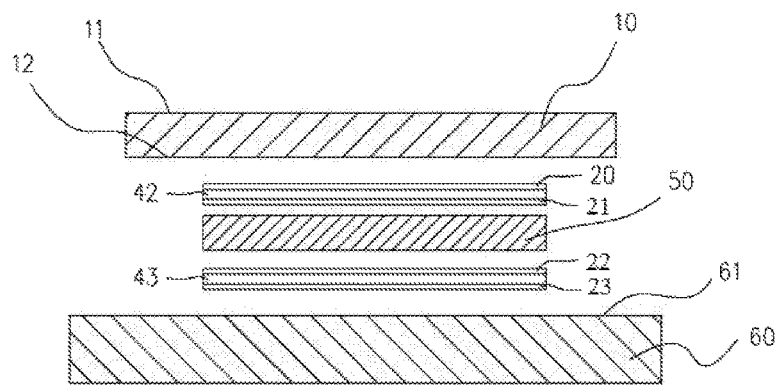
FIG. 8 is a sectional view of a fingerprint sensor in accordance with a seventh implementation of the present disclosure.

FIG. 8 illustrates a fingerprint sensor according to a seventh implementation of the present disclosure. The fingerprint sensor in the seventh implementation is substantially the same as that in the first implementation, and a difference between the fingerprint sensor in the first implementation and the fingerprint sensor in the seventh implementation is that, in the seventh implementation, the substrate layer 40 may include a first substrate layer 42 and a second substrate layer 43. The first substrate layer 42 is provided between the support element 50 and the chip unit 10, and the second substrate layer 43 is provided at a side of the support element 50 away from the chip unit 10. Two opposite sides of the first substrate layer 42 are respectively provided with the first adhesive layer 20 and the third adhesive layer 21, and two opposite sides of the second substrate layer 43 are respectively provided with the fourth adhesive layer 22 and the fifth adhesive layer 23. The fourth adhesive layer 22 has glutinosity which is substantially the same as that of the first adhesive layer 20, or greater than or less than that of the first adhesive layer 20. The fifth adhesive layer 23 has glutinosity which is substantially the same as that of the first adhesive layer 20, or greater than or less than that of the first adhesive layer 20.

Referring still to FIG. 1 and FIG. 2, furthermore, the fingerprint sensor 100 may further include a base plate 60. The support element 50 is fixed to the base plate 60 to support the chip unit 10.

The base plate 60 may be made of metal or plastic. It can be understood that the base plate 60 may be fixed to an inner side of the housing 30 via screws or adhesive, thus the base plate 60 can stably support the chip unit 10. The base plate 60 may include a support surface 61 facing the chip unit 10. A distance L is defined between the support surface 61 and the second surface 12, thus the support element 50 can be stably arranged between the support surface 61 and the second surface 12.

When the fingerprint sensor 100 is applied to the terminal 200, the chip unit 10 can be firstly fixed to the housing 30, then the support element 50 is fixed to the base plate 60, and then the base plate 60 and the support element 50 together are fixed to the inner side of the housing 30, thus the support element 50 can support the chip unit 10. In other implementations, the base plate 60 may be replaced with a pad.

Referring to FIG. 2, FIG. 5, and FIG. 7, in the first implementation, the fourth implementation, and the sixth implementation, the support element 50 is directly fixed to the support surface 61. When an external force is applied to the chip unit 10 to peel off the chip unit 10, the support element 50 and the base plate 60 together are separated from the chip unit 10.

Referring still to FIG. 3 and FIG. 6, in the second implementation and the fifth implementation, the base plate 60 is provided at the side of the substrate layer 40 facing away from the support element 50. The base plate 60 is attached to the substrate layer 40 via the first adhesive layer 20. When an external force is applied to the chip unit 10 to peel off the chip unit 10, the chip unit 10 and the support element 50 together may be separated from the base plate 60.

Referring still to FIG. 4, in the third implementation, the base plate 60 is provided at the side of the substrate layer 40 facing away from the support element 50. The base plate 60 is attached to the substrate layer 40 via the second adhesive layer 41. When an external force is applied to the chip unit 10 to peel off the chip unit 10, the chip unit 10 and the support element 50 together may be separated from the substrate layer 40.

Referring still to FIG. 8, in the seventh implementation, the support element 50 is attached to the support surface 61 via the second substrate layer 43 and the fourth adhesive layer 22 and the fifth adhesive layer 23 respectively coated on the two opposite sides of the second substrate layer 43. Thus, when an external force is applied to the chip unit 10 to peel off the chip unit 10, the chip unit 10 may be separated from the support element 50, and may also be separated from the base plate 60 together with the support element 50.

Referring still to FIG. 1 and FIG. 2, furthermore, the support element 50 may switch between a first state and a second state. A stress provided when the support element 50 is in the first state may be smaller than that provided when the support element 50 is in the second state. When the support element 50 is in the first state, a resistance provided to the chip unit 10 by the support element 50 is reduced. When the support element 50 is the second state, a support force applied to the chip unit 10 by the support element 50 is increased.

When mounting the chip unit 10 and the base plate 60, the distance L between the support surface 61 and the second surface 12 may be changed due to an error generated in mounting process, thus what is needed is that the height h of the support element 50 can be changed to adapt the change of the distance L. Therefore, when mounting the support element 50 and the chip unit 10, the support element 50 is in the first state, that is, the stress of the support element 50 is small. That is, a force between molecules of the support element 50 is small. Thus, the height h of the support element 50 can be changed due to the press of the chip unit 10. At this point, the resistance applied to the chip unit 10 by the support element 50 is smaller than a press force applied to the support element 50 by the chip unit 10, thus the support element 50 cannot jack up the chip unit 10, thereby improving stability performance of the fingerprint sensor 100. When the height h of the support element 50 changes to adapt the distance L, the support element 50 is in the second state, that is, the stress of the support element 50 increases, the force between the molecules of the support element 50 increases, thus the support element 50 can stably support the chip unit 10.

In the implementation, the support element 50 is the adhesive layer. The first state of the support element 50 is a liquid state, and the second state of the support element 50 is a solid state. The support element 50 may be switched between liquid and solid due to change of environment. The support element 50 is made from an epoxy resin material. Before the support element 50 becomes solid, the support element 50 in the first state is placed in a preset position of the support surface 61. Before the support element 50 becomes solid, the preset position of the support surface 61 is aligned with the second surface 12, and the base plate 60 is secured with respect to the chip unit 10, causing the support element 50 to come into contact with the second surface 12. Before the support element 50 becomes solid, a rigid stress does not exist, the support element 50 cannot apply a force to the chip unit 10, thus the support element 50 cannot jack up the chip unit 10. When the support element 50 becomes solid, the rigid stress generates, thus the support element 50 can support the chip unit 10. When the chip unit 10 is pressed, the chip unit 10 is not deformed due to the support element 50, thereby preventing breakage of the chip unit 10, and improving the stability performance of the fingerprint sensor. In other implementations, the support element 50 may be made from photosensitive glue, and also may be made from metallic compound which may be easily solidified.

Figure 9:
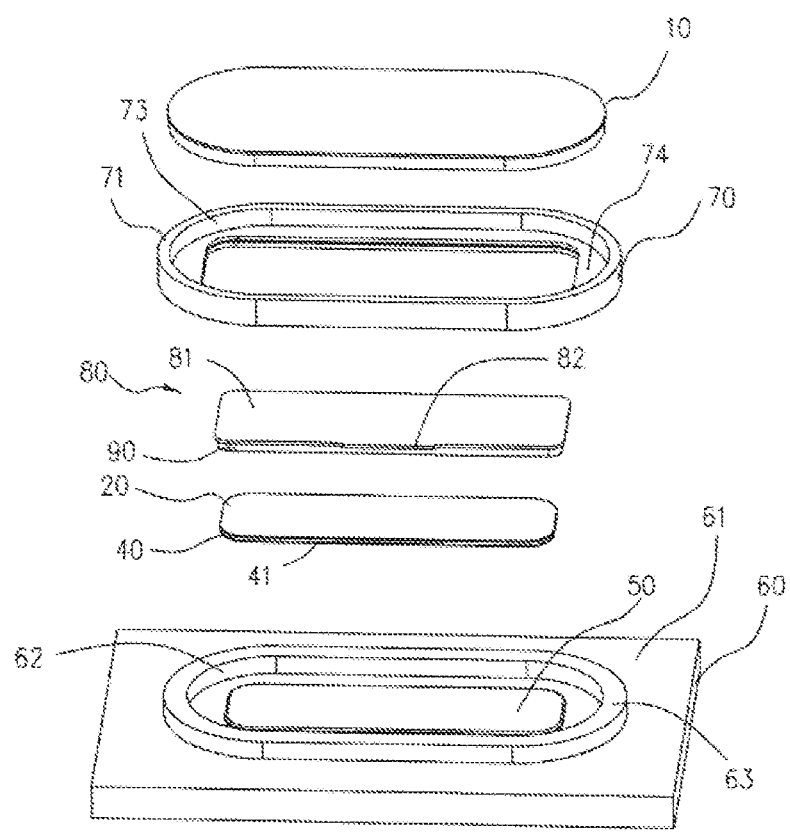
FIG. 9 is a sectional view of a fingerprint sensor in accordance with an eighth implementation of the present disclosure.
Figure 10:
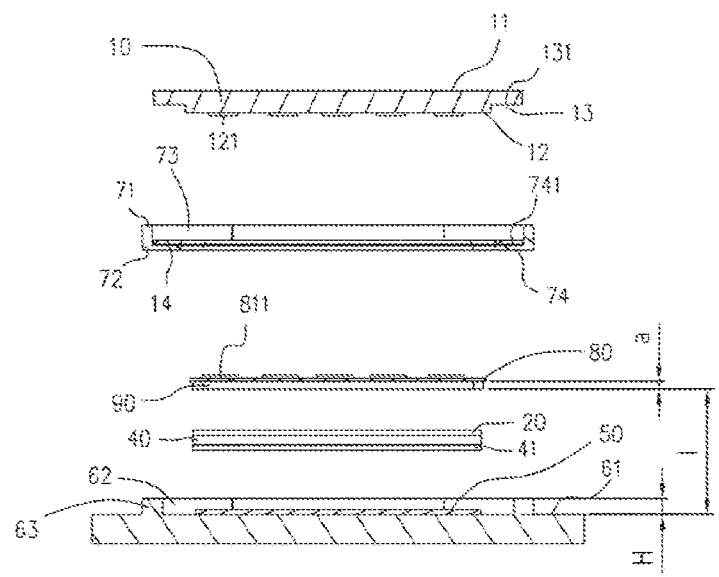
FIG. 10 is a sectional view of the fingerprint sensor of FIG. 9.
Figure 11:
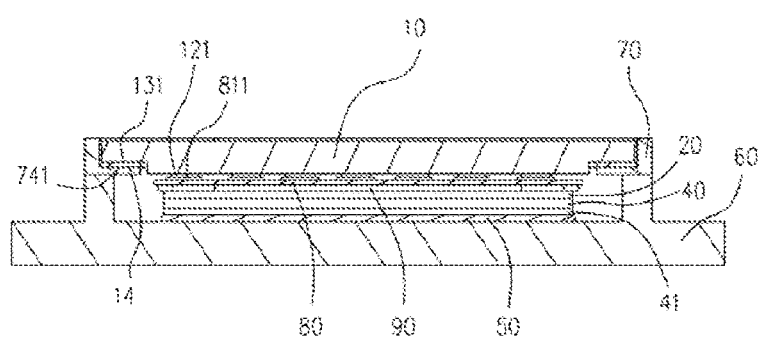
FIG. 11 is an assembled view of the fingerprint sensor of FIG. 9.

Furthermore, referring to FIG. 9, FIG. 10, and FIG. 11, a fingerprint sensor in an eighth implementation is provided. The fingerprint sensor in the eighth implementation is substantially the same as that in the first implementation, and a difference between the fingerprint sensor in the first implementation and the fingerprint sensor in the eighth implementation is that, in the eighth implementation, the fingerprint sensor may further include a protection element 70 detachably connected to the periphery of the chip unit 10. It can be understood that the protection element 70 can be fixed to the housing 30 of the terminal 200. By means of the protection element 70, it is convenient to mount the chip unit 10 to the housing 30.

In the implementation, the protection element 70 is elliptical. The protection element 70 is made of metal material, thus the protection element 70 can protect the chip unit 10. The protection element 70 may include a top surface 71 and a bottom surface 72 opposite to the top surface 71. The protection element 70 may further define the hole 73 extending through the top surface 71 and the bottom surface 72. The chip unit 10 is mounted in the hole 73. A support block 74 protrudes from an inner side of the protection element 70, and is adjacent to the bottom surface 72. The periphery of the chip unit 10 defines a recess portion 13 engageable with the support block 74. The support block 74 may include a bearing surface 741 parallel to the bottom surface 72, thus it is convenient to mount the chip unit 10 in the hole 73. Furthermore, the bearing surface 741 of the support block 74 supports the periphery of the chip unit 10, thus the chip unit 10 can be fixed in the hole 73. The periphery of the chip unit 10 is engageable with the inner side of the hole 73, thus it is convenient to mount the chip unit 10 in the hole 73, friction between the chip unit 10 and the hole 73 can be prevented, and the chip unit 10 can be protected. The first surface 11 of the chip unit 10 is received in the hole 73, and adjacent to the top surface 71, thus it is convenient for a user to touch the first surface 11. The recess portion 13 includes a resistance surface 131 parallel to the first surface 11. The resistance surface 131 is attached to the bearing surface 741 via a sixth adhesive layer 14, for example a release glue layer, thus the periphery of the chip unit 10 is stably arranged on the support block 74, and the chip unit 10 can be stably mounted in the protection element 70. In the implementation, as an error may be generated when forming the recess portion 13, thus the distance between the resistance surface 131 and the second surface 12 may be changed, and the distance from the second surface 12 to the support surface 61 may be changed, that is, the distance L is changed due to the error generated when forming the recess portion 13. Thus, by means of the support element 50, the chip unit 10 can be mounted in the protection element 70. In other implementations, the inner side of the protection element 70 may be engaged with the periphery of the chip unit 10 via latching mechanisms.

Figure 12:
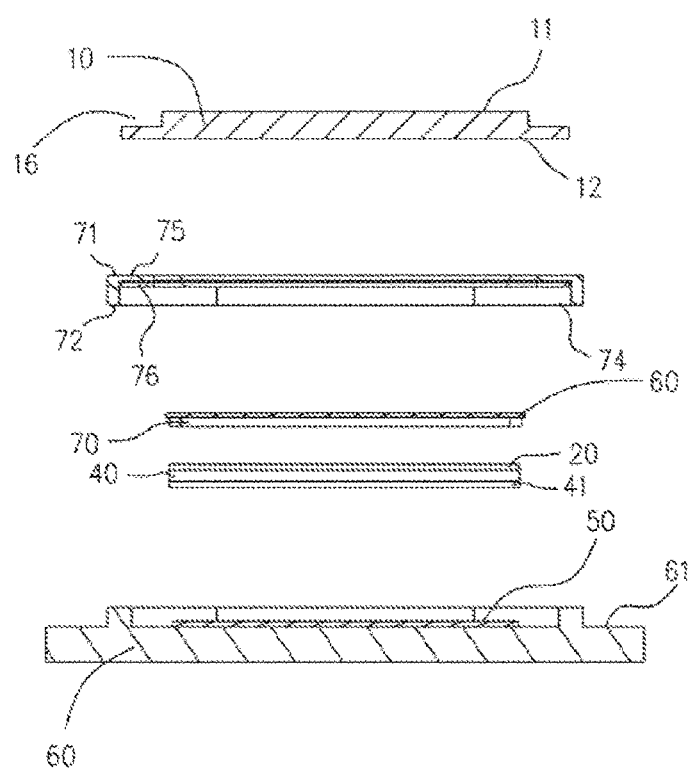
FIG. 12 is a sectional view of a fingerprint sensor in accordance with a ninth implementation of the present disclosure.

Referring to FIG. 12, a fingerprint sensor in a ninth implementation is provided. The fingerprint sensor in the ninth implementation is substantially the same as that in the eighth implementation, and a difference between the fingerprint sensor in the eighth implementation and the fingerprint sensor in the ninth implementation is that, in the ninth implementation, the inner side of the protection element 70 is provided with a cantilever 75. The periphery of the first surface 11 of the chip unit 10 is provided with a latching portion 16 engageable with the cantilever 75. The cantilever 75 is arranged in the inner side of the hole 73, and adjacent to the top surface 71. The cantilever 75 and the latching portion 16 can be fixed together via a seventh adhesive layer 76, for example, via a release glue layer, thus the periphery of the chip unit 10 can be detachably connected to the protection element 70, and it is convenient to peel off the chip unit 10 for replacement. Since the whole chip unit 10 is supported by the support element 50, a resistance force can be applied to the cantilever 75 via the latching portion 16, thereby making the chip unit 10 in the protection element 70 stable.

Figure 13:
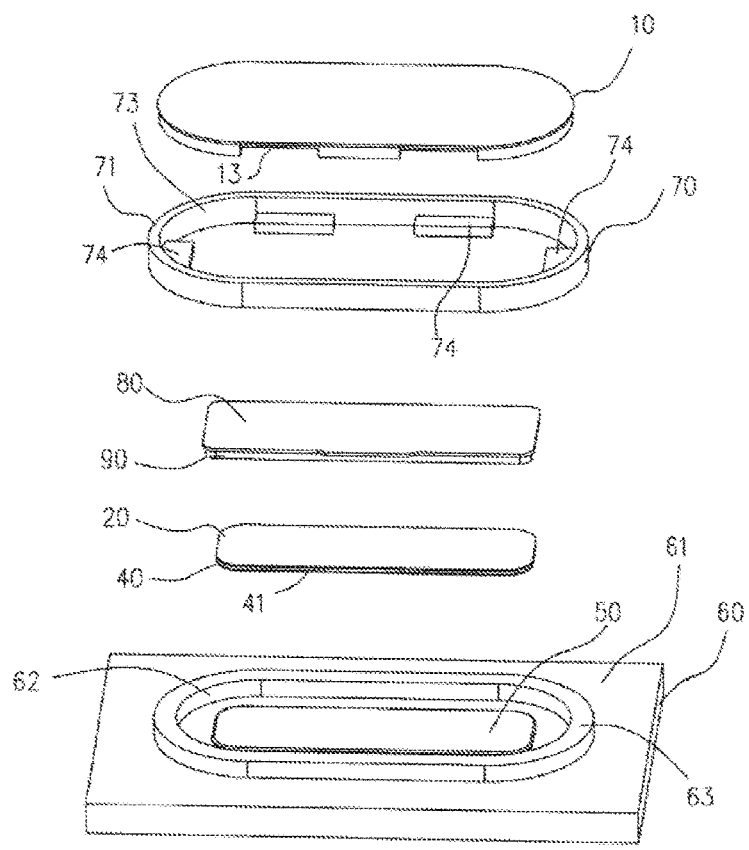
FIG. 13 is a sectional view of a fingerprint sensor in accordance with a tenth implementation of the present disclosure.

Referring to FIG. 13, a fingerprint sensor according to a tenth implementation of the present disclosure is provided. The fingerprint sensor in the tenth implementation is substantially the same as that in the eighth implementation, and a difference between the fingerprint sensor in the eighth implementation and the fingerprint sensor in the tenth implementation is that, in the tenth implementation, multiple support blocks 74 are provided on the inner side of the protection element 70. The support blocks 74 are provided at interval. The periphery of the second surface 12 of the chip unit 10 defines multiple recess portions 13 engageable with the support blocks 74 respectively. The support blocks 74 are equally and circularly arranged along the inner side of the protection element 70, thus the material of the protection element 70 is reduced, and accordingly the cost of the fingerprint sensor 100 is reduced. Furthermore, the recess portions 13 are equally and circularly arranged, the loss of the stress of the periphery of the chip unit 10 is reduced, thereby improving the performance of pressure resistance of the chip unit 10, and preventing breakage of the chip unit 10.

Furthermore, referring still to FIG. 9, FIG. 10, and FIG. 11, in the eighth implementation, the fingerprint sensor may further include a circuit board 80. The circuit board 80 is electrically coupled to the chip unit 10, and arranged between the substrate layer 40 and the second surface 12.

In the implementation, the circuit board 80 is a flexible circuit board. The circuit board 80 may include a connection portion 81 and an extension portion 82 connected to the connection portion 81. The connection portion 81 is electrically coupled to the chip unit 10, and the extension portion 82 may be electrically coupled to a mother board 201 (see FIG. 15) of the terminal 200. The connection portion 81 is provided with weld legs 811, and the second surface 12 is provided with pads 121. The weld legs 811 and the pads 121 are welded together, thus the circuit board 80 is electrically coupled to the chip unit 10. The connection portion 81 of the circuit board 80 is welded to the second surface 12, and then the support element 50 in the liquid state is added to the base plate 60. Before the support element 50 becomes solid, the first adhesive layer 20 is provided to the support element 50. The base plate 60 and the protection element 70 are fixed together to cause the support element 50 to come into contact with the circuit board 80. After the support element 50 becomes solid, the support element 50 supports the circuit board 80 and the chip unit 10. Certainly, in other implementations, the support element 50 may be in contact with the second surface 12 and the connection portion 81, and the support element 50 supports the circuit board 80 and the chip unit 10, thereby improving stability performance of the fingerprint sensor 100. In other implementations, the circuit board 80 may also be a printed circuit board or a rigid-flexible circuit board. The support element 50 is fixed between the base plate 60 and the printed circuit board or the rigid-flexible circuit board.

Furthermore, in the eighth implementation, the fingerprint sensor 100 may further include a reinforcement plate 90. The reinforcement plate 90 is attached to the side of the circuit board 80 facing away from the chip unit 10.

In the implementation, the reinforcement plate 90 is made of metal material, such as a steel plate. The reinforcement plate 90 is attached to the circuit board 80. The width of the reinforcement plate 90 is substantially equivalent to that of the second surface 12. The reinforcement plate 90 supports the circuit board 80 to improve the rigidity of the circuit board 80, thereby preventing breakage of the circuit board 80. The reinforcement plate 90 is firstly attached to the side of the circuit board 80 facing away from the chip unit 10, and then the support element 50 in the liquid state is added to the base plate 60. Before the support element 50 becomes solid, the base plate 60 and the protection element 70 are fixed together to cause the support element 50 to come into contact with the reinforcement plate 90. When the support element 50 becomes solid, the support element 50 supports the reinforcement plate 90, the circuit board 80, and the chip unit 10, thereby improving the stability performance of the fingerprint sensor 100. In other implementations, the reinforcement plate 90 may be a resin plate.

Furthermore, in the eighth implementation, the base plate 60 is provided with a boss 63 for supporting the protection element 70. The boss 63 defines a receiving cavity 62 with an opening facing the second surface 12. The support element 50 is received in the receiving cavity 62.

In the implementation, the receiving cavity 62 is rectangular. The opening of the receiving cavity 62 faces the chip unit 10. By receiving the support element 50 in the receiving cavity 62, the support element 50 can be raised to a certain height, thus the support element 50 and the first adhesive layer 20 can come into contact with the reinforcement plate 90. Since the circuit board 80 and the reinforcement plate 90 are laminated on the second surface 12, the reinforcement plate 90 may be exposed out of the hole 73, thus the reinforcement plate 90 can be received in the receiving cavity 62, and the support element 50 received the receiving cavity 62 and the first adhesive layer 20 can come into contact with the reinforcement plate 90. The reinforcement plate 90 is firstly attached to the circuit board 80, then the receiving cavity 62 is filled with the support element 50 that is in the liquid state, and then the first adhesive layer 20 is applied to the support element 50. The chip unit 10, the protection element 70, the circuit board 80, and the reinforcement plate 90 together are covered by the base plate 60, so that the reinforcement plate 90 is received in the receiving cavity 62, and the reinforcement plate 90 comes into contact with the first adhesive layer 20. Thus, when the support element 50 becomes solid, the support element 50 can support the reinforcement plate 90, and as the support element 50 is received in the receiving cavity 62, the support element 50 that is in the liquid state cannot flow out. Furthermore, when the chip unit 10, the circuit board 80, and the reinforcement plate 90 together are separated from the support element 50, the chip unit 10 can be replaced. In other implementation, multiple receiving cavities may be defined, and multiple reinforcement plates are attached to the circuit board 80. Each reinforcement plate is received in the corresponding receiving cavity.

Furthermore, since the receiving cavity 62 is defined in the boss 63, the depth of the receiving cavity 62 is enough to receive the support element 50. When various errors are generated in the process of forming the recess portion 13, the reinforcement plate 90 can be still received in the receiving cavity 62, thus the support element 50 can support the chip unit 10.

Figure 14:
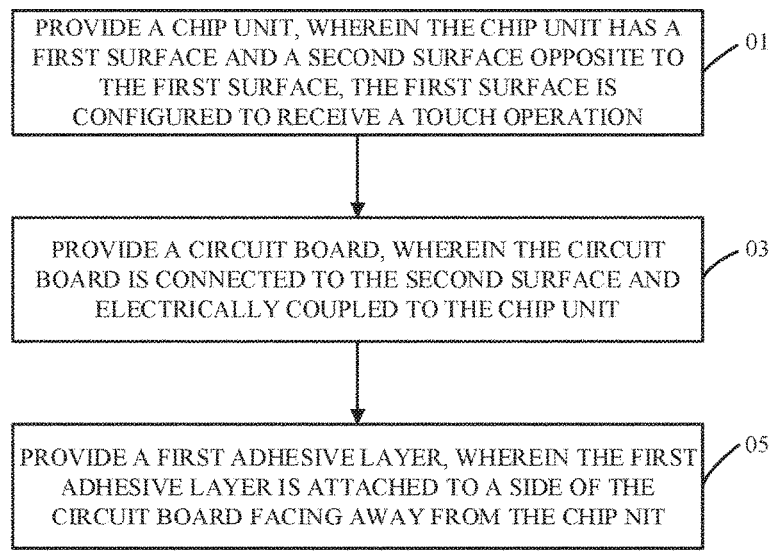
FIG. 14 is a flow chart of a method for manufacturing a fingerprint sensor in accordance with an implementation of the present disclosure.

The present disclosure further provides a method for manufacturing the fingerprint sensor. Referring to FIG. 9, FIG. 10, and FIG. 14, the method may include the follows.

At block 01, the chip unit 10 is provided. The chip unit 10 has the first surface 11 and the second surface 12 opposite to the first surface 11. The first surface 11 is configured to receive a touch operation. The second surface 12 is provided with the pads 121. The chip unit 10 is electrically coupled to another element via the pads 121.

At block 03, the circuit board 80 is provided. The circuit board 80 is connected to the second surface 12.

In the implementation, the circuit board 80 is a flexible circuit board. The circuit board 80 includes the weld legs 811. The weld legs 811 and the pads 121 are welded together, so that the circuit board 80 is electrically coupled to the chip unit 10. The reinforcement plate 90 is provided on the side of the circuit board 80 facing away from the chip unit 10 to increase the rigidity of the circuit board 80. Certainly, in other implementations, the circuit board 80 may be a printed circuit board, and the reinforcement plate 90 may not be needed.

At block 05, the first adhesive layer 20 is provided. The first adhesive layer 20 is attached to the side of the circuit board 80 away from the chip unit 10.

In the implementation, the first adhesive layer 20 is coated on the first side of the substrate layer 40. The substrate layer 40 is attached to the circuit board 80 via the first adhesive layer 20.

When providing the first adhesive layer 20, the support element 50 and the base plate 60 are further provided. The support element 50 is attached to the second side of the substrate layer 40. The base plate 60 is attached to the second surface 12 via the support element 50, the substrate layer 40, and the circuit board 80. The base plate 60 is fixed to the inner side of the housing 30. The support element 50 may be the adhesive layer. Before mounting the base plate 60 and the chip unit 10, the support element 50 is liquid, and the support element 50 is applied to the base plate 60. The substrate layer 40 is then attached to the support element 50. The second adhesive layer 41 coated on the substrate layer 40 is attached to the support element 50. The first adhesive layer 20 coated on the substrate layer 40 faces the chip unit 10. The chip unit 10, the circuit board 80, and the reinforcement plate 90 together are then attached to the first adhesive layer 20, and accordingly the first adhesive layer 20 and the support element 50 are pressed. After mounting the base plate 60 and the chip unit 10, the support element 50 is attached to the side of the substrate layer 40 facing away from the chip unit 10 via the second adhesive layer 41. When the support element 50 becomes solid, the support element 50 and the first adhesive layer 20 together support the chip unit 10.

Figure 15:
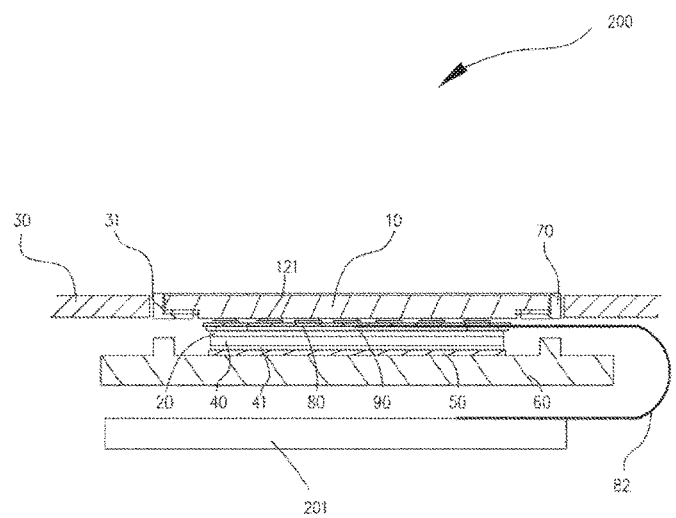
FIG. 15 is a sectional view of a terminal in accordance with an implementation of the present disclosure.

Referring to FIG. 15, the present disclosure further provides the terminal 200. The terminal 200 may include the fingerprint sensor 100. The terminal 200 may further include the housing 30 and the mother board 201. The chip unit 10 is fixed to the housing 30. The first surface 11 of the chip unit 10 faces the outside of the housing 30. The base plate 60 is fixed within the housing 30.

In the implementation, the housing 30 defines the hole 31. The protection element 70 is fixed in the hole 31. The base plate 60 is fixed to the inner side of the housing 30. The mother board 201 is fixed within the housing 30, and is electrically coupled to the circuit board 80. The housing 30 may be a front cover of a display unit of the terminal 200. The housing 30 may be constructed by a cover plate, a touch panel, and a display unit that are laminated sequentially. Light can be transmitted through the cover plate. The protection element 70 and the housing 30 are integrally formed, thus the protection element 70 can be stably fixed in the hole 31. The base plate 60 can be fixed to the inner side of the housing 30 via adhesive or screws, thus the base plate 60 and the support element 50 can stably support the chip unit 10. After the extension portion 82 of the circuit board 80 is bent, the extension portion 82 can be electrically coupled to the mother board 201, so that the chip unit 10 can be electrically coupled to the mother board 201 via the circuit board 80. In other implementations, the housing 30 may be a rear cover of the terminal 200.

While the present disclosure has been described in detail above with reference to the exemplary implementations, the scope of the present disclosure is not limited thereto. As will occur to those skilled in the art, the present disclosure is susceptible to various modifications and changes without departing from the spirit and principle of the present disclosure. Therefore, the scope of the present disclosure shall be determined by the scope of the claims.

What is claimed is:

1. A fingerprint sensor, comprising:
   a chip unit having a first surface and a second surface opposite the first surface, the first surface being configured to receive a touch operation;
   a first adhesive layer;
   a second adhesive layer;
   an isolation element arranged on the second surface;
   a substrate layer having a first side and a second side opposite the first side, the first side being provided with the second adhesive layer and attached to the isolation element via the second adhesive layer, and the second side being provided with the first adhesive layer; and
   a support element attached to the substrate layer to support the chip unit;
   the substrate layer being attached to the support element via the first adhesive layer, and the second adhesive layer having a larger glutinosity than the first adhesive layer.

2. The fingerprint sensor of claim 1, wherein the substrate layer comprises a first substrate layer and a second substrate layer, the first substrate layer is attached to a side of the support element facing the chip unit, and the second substrate layer is attached to a side of the support element away from the chip unit.

3. The fingerprint sensor of claim 1, further comprising a base plate, wherein the support element is attached to the base plate to support the chip unit.

4. The fingerprint sensor of claim 1, wherein the support element is configured to be switched between a liquid state and a solid state.

5. The fingerprint sensor of claim 1, wherein the fingerprint sensor further comprises a circuit board arranged between the substrate layer and the second surface, and electrically coupled to the chip unit.

6. A terminal, comprising:
   a chip unit having a first surface exposed outside of the terminal, and a second surface opposite the first surface;
   a circuit board electrically coupled to the chip unit; and
   a first adhesive layer;
   a second adhesive layer;
   a support element; and
   a substrate layer having a first side and a second side opposite the first side, the first side being provided with the first adhesive layer and attached to the second surface via the first adhesive layer, and the second side being provided with the second adhesive layer and attached to the support element via the second adhesive layer;
   the second adhesive layer has a larger glutinosity than the first adhesive layer.

7. The terminal of claim 6, wherein the support element is configured to be switched between a liquid state and a solid state.

8. The terminal of claim 6, further comprising a protection element, wherein the chip unit has a peripheral side detachably connected to the protection element.

9. The terminal of claim 6, wherein the terminal further comprises a mother board electrically coupled to the chip unit via the circuit board.

10. A method for manufacturing a fingerprint sensor, comprising:
    providing a chip unit, wherein the chip unit comprises a first surface and a second surface opposite the first surface, the first surface being configured to receive a touch operation;
    providing a first adhesive layer;
    providing a second adhesive layer;
    providing an isolation element arranged on the second surface;
    providing a substrate layer having a first side and a second side opposite the first side, the first side being provided with the second adhesive layer and attached to the isolation element via the second adhesive layer, and the second side being provided with the first adhesive layer; and
    providing a support element attached to the substrate layer to support the chip unit;
    the substrate layer being attached to the support element via the first adhesive layer, and the second adhesive layer having a larger glutinosity than the first adhesive layer.

* * * * *